United States Patent [19]

Owen et al.

[11] Patent Number: 4,471,147

[45] Date of Patent: Sep. 11, 1984

[54] OLEFIN FRACTIONATION AND CATALYTIC CONVERSION SYSTEM

[75] Inventors: Hartley Owen, Belle Mead; Chung H. Hsia, Matawan; Bernard S. Wright, East Windsor, all of N.J.

[73] Assignee: Mobil Oil Corporation, New York, N.Y.

[21] Appl. No.: 508,959

[22] Filed: Jun. 29, 1983

[51] Int. Cl.[3] .................... C07C 2/02

[52] U.S. Cl. .................... 585/519; 585/533

[58] Field of Search .................... 585/519, 533

[56] References Cited

U.S. PATENT DOCUMENTS

| | | | |
|---|---|---|---|
| 2,938,865 | 5/1960 | Moyer | 208/341 |
| 2,939,834 | 6/1960 | Evans | 208/101 |
| 3,542,892 | 11/1970 | Stoker et al. | 585/451 |
| 4,182,922 | 1/1980 | Schick et al. | 585/517 |

*Primary Examiner*—Curtis R. Davis

*Attorney, Agent, or Firm*—A. J. McKillop; M. G. Gilman; L. G. Wise

[57] ABSTRACT

A continuous catalytic process for converting an olefinic feedstock comprising ethylene and $C_3+$ olefins to heavier liquid hydrocarbon product comprising the steps of (a) prefractionating the olefinic feedstock to obtain a gaseous stream rich in ethylene and a liquid stream containing $C_3+$ olefins;

(b) vaporizing and contacting the liquid stream from the prefractionating step with hydrocarbon conversion oligomerization catalyst in a catalytic reactor system to provide a heavier hydrocarbon effluent stream comprising distillate, gasoline and lighter hydrocarbons;

(c) fractionating the effluent stream to recover distillate, gasoline and lighter hydrocarbons separately;

(d) recycling at least a portion of the recovered gasoline as a liquid sorption stream to prefractionating step (a); and (e) further reacting the recycled gasoline together with sorbed $C_3+$ olefins in the catalytic reactor system of step (b).

9 Claims, 3 Drawing Figures

OLEFIN FRACTIONATION AND CATALYTIC CONVERSION SYSTEM

FIELD OF THE INVENTION

This invention relates to processes and apparatus for converting olefins to higher hydrocarbons, such as gasoline-range and/or distillate-range fuels. In particular it relates to techniques for operating a catalytic reactor system and feedstock fractionation system.

BACKGROUND OF THE INVENTION

Improved catalytic hydrocarbon conversion processes have created interest in utilizing olefinic feedstocks, such as petroleum refinery streams rich in lower olefins, for producing $C_5+$ gasoline, diesel fuel, etc. In addition to the basic work derived from ZSM-5 type zeolite catalyst research, a number of discoveries have contributed to the development of a new industrial process, known as Mobil Olefins to Gasoline/Distillate ("MOGD"). This process has significance as a safe, environmentally acceptable technique for utilizing refinery streams that contain lower olefins, especially $C_2$–$C_5$ alkenes. This process may supplant conventional alkylation units. In U.S. Pat. Nos. 3,960,978 and 4,021,502, Plank, Rosinski and Givens disclose conversion of $C_2$–$C_5$ olefins, alone or in admixture with paraffinic components, into higher hydrocarbons over crystalline zeolites having controlled acidity. Garwood et al have also contributed improved processing techniques to the MOGD system, as in U.S. Pat. Nos. 4,150,062, 4,211,640 and 4,227,992. The above-identified disclosures are incorporated herein by reference.

Conversion of lower olefins, especially propene and butenes, over H-ZSM-5 is effective at moderately elevated temperatures and pressures. The conversion products are sought as liquid fuels, especially the $C_5^{30}$ aliphatic and aromatic hydrocarbons. Olefinic gasoline is produced in good yield by the MOGD process and may be recovered as a product or recycled to the reactor system for further conversion to distillate-range products.

As a consequence of the relatively low reactivity of ethylene with known zeolite oligomerization catalysts (about 10–20% conversion for HZSM-5), distillate-mode reactor systems designed to completely convert a large ethylenic component of feedstock would require much larger size than comparable reactor systems for converting other lower olefins. Recycle of a major amount of ethylene from the reactor effluent would result in significant increases in equipment size. By contrast, propene and butene are converted efficiently, 75 to 95% or more in a single pass, under catalytic conditions of high pressure and moderate pressure used in distillate mode operation.

Ethylene has substantial value as a feedstock for polymer manufacture or other industrial processes, and can be recovered economically. It has been found that an olefin-to-distillate process utilizing $C_2$–$C_4$ olefinic feedstock can be operated to prefractionate the feedstock for ethylene recovery and catalytic conversion of the $C_3+$ olefinic components.

Olefinic feedstocks may be obtained from various sources, including fossil fuel processing streams, such as gas separation units, cracking of $C_2+$ hydrocarbons, coal byproducts, alcohol conversion, and various synthetic fuel processing streams. Cracking of ethane and conversion of effluent is disclosed in U.S. Pat. No. 4,100,218 and conversion of ethane to aromatics over Ga-ZSM-5 is disclosed in U.S. Pat. No. 4,350,835. Olefinic effluent from fluidized catalytic cracking of gas oil or the like is a valuable source of olefins, mainly $C_3$–$C_4$ olefins, suitable for exothermic conversion according to the present MOGD process. It is an object of the present invention to provide a unique prefractionation system for recovery of valuable ethylene and economic operation of an integrated MOGD type reactor system.

SUMMARY OF THE INVENTION

A novel technique has been found for separating and condensing olefins in a continuous catalytic process. Methods and apparatus are provided for converting a fraction of olefinic feedstock comprising ethylene and $C_3+$ olefins to heavier liquid hydrocarbon product. It is an object of this invention to effect conversion by (a) prefractionating the olefinic feedstock to obtain a gaseous stream rich in ethylene and a liquid stream containing $C_3+$ olefins; (b) vaporizing and contacting the liquid stream from the prefractionating step with hydrocarbon conversion oligomerization catalyst in a catalytic reactor system to provide a heavier hydrocarbon effluent stream comprising distillate, gasoline and lighter hydrocarbons; (c) fractionating the effluent stream to recover distillate, gasoline and lighter hydrocarbons separately; (d) recycling at least a portion of the recovered gasoline as a liquid sorption stream to the prefractionating unit; and (e) further reacting the recycled gasoline together with sorbed $C_3+$ olefins in the catalytic reactor system.

A continuous process has been designed to achieve these objectives for an exothermic reactor system with efficient heat exchange, product recovery and recycle system. Advantageously, exothermic heat is recovered from the reactor effluent and utilized to heat one or more fractionation system liquid streams, such as a sorption prefractionator reboiler stream.

Typically, the olefinic stock consists essentially of $C_2$–$C_6$ aliphatic hydrocarbons containing a major fraction of monoalkenes in the essential absence of dienes or other deleterious materials. The process may employ various volatile lower olefins as feedstock, with oligomerization of $C_3+$ alpha-olefins being preferred for either gasoline or distillate production. Preferably the olefinic feedstream contains about 50 to 75 mole % $C_3$–$C_5$ alkenes.

These and other objects and featues of the novel MOGD system will be seen in the following description of the drawing.

DESCRIPTION OF PREFERRED EMBODIMENTS

Figure 1:
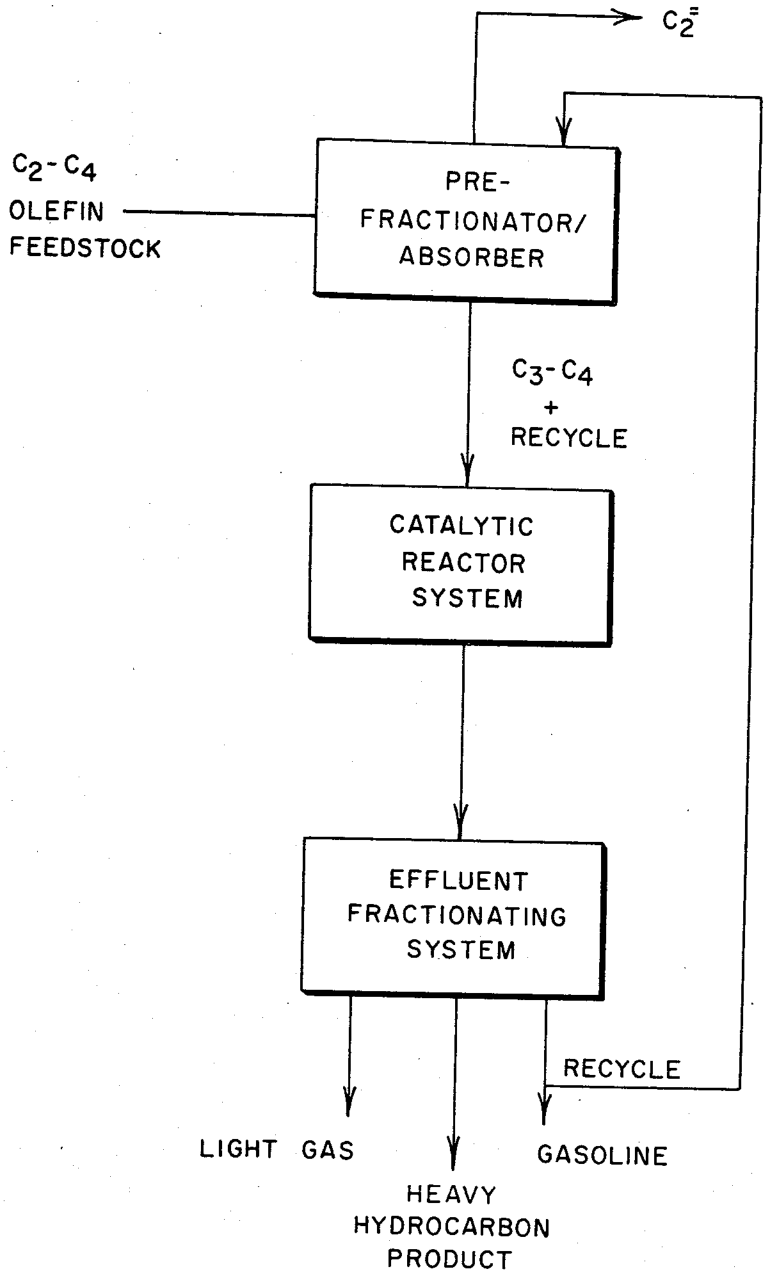
FIG. 1 is a simplified process flow diagram showing relationships between the major unit operations.

The overall relationship of the invention to a petroleum refinery is depicted in FIG. 1. Various olefinic and paraffinic light hydrocarbon streams may be involved in the reactor or fractionation subsystems. An olefinic feedstock, such as $C_2$–$C_4$ olefins derived from catalytic cracker (FCC) effluent, may be emplpoyed as a feedstock rich in ethene, propene, butenes, etc. for the process. The prefractionator/absorber unit separates the feedstock into a relatively pure ethene gas product and $C_3$+ liquid comprising the rich sorbent. Following reaction at elevated temperature and pressure over a shape selective catalyst, such as ZSM-5 or the like, the reactor system effluent is fractionated. The fractionation subsystem has been devised to yield three main liquid product streams—LPG (mainly $C_3$-$C_4$ alkanes), gasoline boiling range hydrocarbons ($C_5$ to 330° F.) and distillate range heavier hydrocarbons (330° F.+). Optionally, all or a portion of the olefinic gasoline range hydrocarbons from the product fractionator unit may be recycled for further conversion to heavier hydrocarbons in the distillate range. This may be accomplished by combining the recycle gasoline with $C_5$+ olefin feedstock in the prefractionation step prior to heating the combined streams.

Process conditions, catalysts and equipment suitable for use in the MOGD process are described in U.S. Pat. No. 3,960,978 (Givens et al), U.S. Pat. No. 4,021,502 (Plank et al), and U.S. Pat. No. 4,150,062 (Garwood et al). Hydrotreating and recycle of olefinic gasoline are disclosed in U.S. Pat. No. 4,211,640 (Garwood and Lee). Other pertinent disclosures include U.S. Pat. No. 4,227,992 (Garwood and Lee) and U.S. patent application Ser. No. 488,334, filed Apr. 26, 1983 (Owen et al.) relating to catalytic processes for converting olefins to gasoline/distillate. The above disclosures are incorporated herein by reference.

CATALYST

The catalytic reactions employed herein are conducted, preferably in the presence of medium pore silicaceous metal oxide crystalline catalysts, such as acid ZSM-5 type zeolites catalysts. These materials are commonly referred to as aluminosilicates or porotectosilicates; however, the acid function may be provided by other tetrahedrally coordinated metal oxide moieties, especially Ga, B, Fe or Cr. Commercially available aluminosilicates such as ZSM-5 are employed in the operative embodiments; however, it is understood that other silicaceous catalysts having similar pore size and acidic function may be used within the inventive concept.

The catalyst materials suitable for use herein are effective in oligomerizing lower olefins, especially propene and butene-1 to higher hydrocarbons. The unique characteristics of the acid ZSM-5 catalyts are particularly suitable for use in the MOGD system. Effective catalysts include those zeolites disclosed in U.S. Pat. No. 4,430,516 and application Ser. No. 408,954 filed Aug. 17, 1982 (Koenig and Degnan), which relate to conversion of olefins over large pore zeolites. A preferred catalyst material for use herein is an extrudate (1.5 mm) comprising 65 weight % HZSM-5 and 35% alumina binder, having an acid cracking activity (α) of about 160 to 200.

The members of the class of crystalline zeolites for use in this invention are characterized by a pore dimension greater than about 5 Angstroms, i.e., it is capable of sorbing paraffins having a single methyl branch as well as normal paraffins, and it has a silica to alumina mole ratio of at least 12.

Although such crystalline zeolites with a silica to alumina mole ratio of at least about 12 are useful, it is preferred to use zeolites having higher ratios of at least about 30. In some zeolites, the upper limit of silica to alumina mole ratio is unbounded, with values of 30,000 and greater.

The members of the class of zeolites for use herein are exemplified by ZSM-5, ZSM-5/ZSM-11 intermediate, ZSM-11, ZSM-12, ZSM-23, ZSM-35, ZSM-38, ZSM-48 and other similar materials. U.S. Pat. No. 3,702,886 describing and claiming ZSM-5 is incorporated herein by reference. Also, U.S. Pat. No. Re. 29,948 described and claiming a crystalline material with an X-ray diffraction pattern of ZSM-5, is incorporated herein by reference as is U.S. Pat. No. 4,061,724 describing a high silica ZSM-5 referred to as "silicate" in such patent. The ZSM-5/ZSM-11 intermediate is described in U.S. Pat. No. 4,229,424. ZSM-11 is described in U.S. Pat. No. 3,709,979. ZSM-12 is described in U.S. Pat. No. 3,832,449. ZSM-23 is described in U.S. Pat. No. 4,076,842. ZSM-35 is described in U.S. Pat. No. 4,016,245. ZSM-38 is described in U.S. Pat. No. 4,046,859. The entire contents of the above identified patents are incorporated herein by reference. ZSM-48 is more particularly described in U.S. Pat. No. 4,375,573, the entire contents of which are incorporated herein by reference.

The zeolites used in additive catalysts in this invention may be in hydrogen form or they may be base exchanged or impregnated to contain a rare earth cation complement. Such rare earth cations comprise Sm, Nd, Pr, Ce and La. It is desirable to calcine the zeolite after base exchange.

The catalyst and separate additive composition for use in this invention may be prepared in various ways. They may be separately prepared in the form of particles such as pellets or extrudates, for example, and simply mixed in the required proportions. The particle size of the individual component particles may be quite small, for example from about 10 to about 150 microns, when intended for use in fluid bed operation, or they may be as large as up to about 1-10 mm for fixed bed operation. The components may be mixed as powders and formed into pellets or extrudate, each pellet containing both components in substantially the required proportions. It is desirable to incorporate the zeolite component of the separate additive composition in a matrix. Such matrix is useful as a binder and imparts greater resistance to the catalyst for the severe temperature, pressure and velocity conditions encountered in many cracking processes. Matrix materials include both synthetic and natural substances. Such substances include clays, silica and/or metal oxides. The latter may be either naturally occurring or in the form of gelatinous precipitates, sols or gels including mixtures of silica and metal oxides. Frequently, zeolite materials have been incorporated into naturally occurring clays, e.g. bentonite and kaolin.

A particularly advantageous form of the catalyst is an extruded pellet having a diameter of about 1-3 mm, made by mixing steamed zeolite crystals eg. silica:alumina=70:1-500:1 with α-alumina monohydrate in a proportion of about 2:1 and calcining the formed material to obtain an extrudate having a void fraction of about 30-40%, preferably about 36%.

GENERAL PROCESS DESCRIPTION

Figure 2:
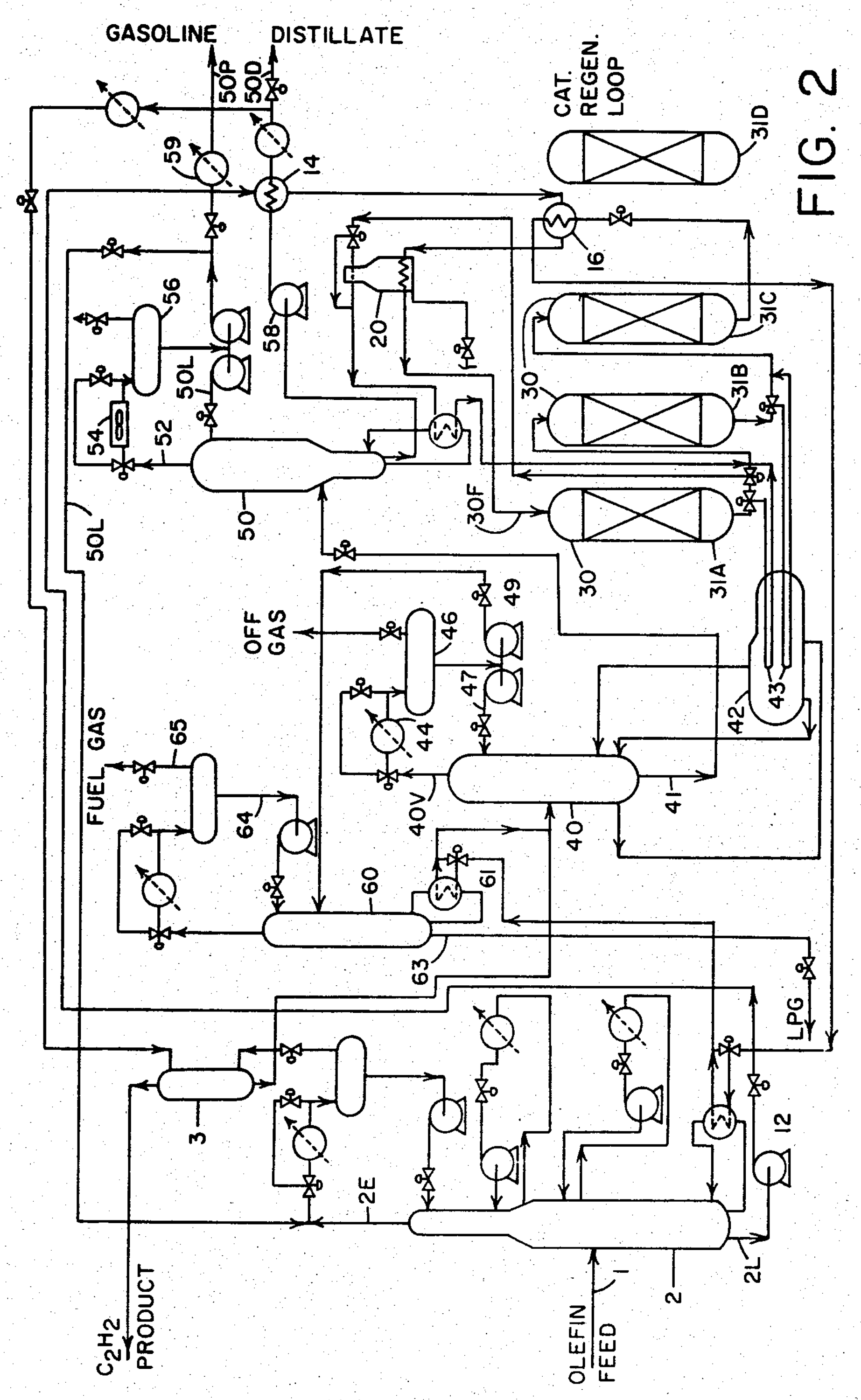
FIG. 2 is a schematic system diagram showing a process equipment and flow line configuration for a preferred embodiment.

Referring to FIG. 2, olefinic feedstock is supplied to the plant through fluid conduit 1 under steady stream conditions. The olefins are separated in prefractionator 2 to recover an ethylene-rich stream 2E and liquid hydrocarbon stream 2L containing $C_3$+ feedstock components, as described in detail hereafter. This $C_3^{30}$ feedstream is pressurized by pump 12 and then sequentially heated by passing through indirect heat exchange units 14, 16, and furnace 20 to achieve the temperature for catalytic conversion in reactor system 30, including plural reactor vessels 31A, B, C, etc.

The reactor system section shown consists of 3 downflow fixed bed, series reactors on line with exchanger cooling between reactors. The reactor configuration allows for any reactor to be in any position, A, B or C. The reactor in position A has the most aged catalyst and the reactor in position C has freshly regenerated catalyst. The cooled reactor effluent is fractionated first in a debutanizer 40 to provide lower aliphatic liquid recycle and then in splitter unit 50 which not only separates the debutanizer bottoms into gasoline and distillate products but provides liquid gasoline recycle.

The gasoline recycle is not only necessary to produce the proper distillate quality but also limits the exothermic rise in temperature across each reactor to less than 30° C. Change in recycle flow rate is intended primarily to compensate for gross changes in the feed non-olefin flow rate. As a result of preheat, the liquid recycle are substantially vaporized by the time that they reach the reactor inlet. The following is a description of the process flow in detail.

Sorbed $C_3+$ olefin combined with olefinic gasoline is pumped up to system pressure by pump 12 and is combined with gasoline recycle after that stream has been pumped up to system pressure by pump 58. The combined stream ($C_3+$ feed plus gasoline recycle) after preheat is routed to the inlet 30F of the reactor 31A of system 30. The combined stream (herein designated as the reactor feedstream) is first preheated against the splitter tower 50 effluent in exchanger 14 (reactor feed/splitter tower bottoms exchanger) and then against the effluent from the reactor in position C, in exchanger 16 (reactor feed/reactor effluent exchanger). In the furnace 20, the reactor feed is heated to the required inlet temperature for the reactor in position A.

Because the reaction is exothermic, the effluents from the reactors in the first two positions A, B are cooled to the temperature required at the inlet of the reactors in the last two positions, B, C, by partially reboiling the debutanizer, 40. Temperature control is accomplished by allowing part of the reactor effluents to bypass the reboiler 42. Under temperature control of the bottom stage of the sorption fractionator 2, energy for reboiling is provided by at least part of the effluent from the reactor 31 in position C.

After heating fractionator 2 reboilant, the reactor effluent reboils deethanizer bottoms 61 and is then routed to the debutanizer 40 which is operated at a pressure which completely condenses the debutanizer tower overhead 40V by cooling in condenser 44. The liquid from debutanizer overhead accumulator 46 provides the tower reflux 47, and feed to the deethanizer 60, which, after being pumped to the deethanizer pressure by pump 49 is sent to the deethanizer 60. The deethanizer accumulator overhead 65 is routed to the fuel gas system. The accumulator liquid 64 provides the tower reflux. The bottoms stream 63 (LPG product) may be sent to an unsaturated gas plant or otherwise recovered.

The bottoms stream 41 from the debutanizer 40 is sent directly to the splitter, 50 which splits the $C_5+$ material into $C_5$-330° F. gasoline (overhead liquid product and recycle) and 330° F.+ distillate (bottoms product). The splitter tower overhead stream 52 is totally condensed in the splitter tower overhead condenser 54. The liquid from the overhead accumulator 56 provides the tower reflux 50L, the gasoline product 50P and the specified gasoline recycle 50R under flow control, pressurized by pump 58 for recycle. After being cooled in the gasoline product cooler 59, the gasoline product is sent to the gasoline pool. The splitter bottoms fraction is pumped to the required pressure by pump 58 and then preheats the reactor feed stream in exchanger 14. Finally, the distillate product 50D is cooled to ambient temperature before being hydrotreated to improve its cetane number.

From an energy conservation standpoint, it is advantageous to reboil the debutanizer 40 using reactor effluent as opposed to using a fired reboiler. A kettle reboiler 42 containing 2 U-tube exchangers 43 in which the reactor 31 effluents are circulated is a desirable feature of the system. Liquid from the bottom stage of debutanizer 40 is circulated in the shell side.

In order to provide the desired quality and rate for gasoline recycle, it is necessary to fractionate the reactor effluent. Phase separators do not give the proper separation of the reactor effluent to meet the quality standards and rate for both liquid recycles. For example, the gasoline recycle would carry too much distillate and lights. Consequently, it would be difficult to properly control the liquid recycle if separators were employed.

The product fractionation units 40, 50, and 60 may be a tray-type design or packed column. The splitter distillation tower 50 is preferably operated at substantially atmospheric pressure to avoid excessive bottoms temperature, which might be deleterious to the distillate product. The fractionation equipment and operating techniques are substantially similar for each of the major stills 40, 50, 60, with conventional plate design, reflux and reboiler components. The fractionation sequence and heat exchange features of the present system are operatively connected in an efficient MOGD system provide significant economic advantages.

MOGD operating modes may be selected to provide maximum distillate product by gasoline recycle and optimal reactor system conditions. Operating examples are given for distillate mode operation, utilizing as the olefinic feedstock a pressurized stream olefinic feedstock (about 1200 kPa) comprising a major weight and mole fraction of $C_3{=}/C_4{=}$. The adiabatic exothermic oligomerization reaction conditions are readily optimized at elevated temperature and/or pressure to increase distillate yield or gasoline yield as desired, using HZSM-5 type catalyst. Particular process parameters such as space velocity, maximum exothermic temperature rise, etc. may be optimized for the specific oligomerization catalyst employed, olefinic feedstock and desired product distribution.

DISTILLATE MODE REACTOR OPERATION

A typical distillate mode multi-zone reactor system employs inter-zone cooling, whereby the reaction exotherm can be carefully controlled to prevent excessive temperature above the normal moderate range of about 190° to 315° C. (375°-600° F.).

Advantageously, the maximum temperature differential across any one reactor is about 30° C. ($\Delta T \sim 50°$ F.) and the space velocity (LHSV based on olefin feed) is about 0.5 to 1. Heat exchangers provide inter-reactor cooling and reduce the effluent to fractionation temperature. It is an important aspect of energy conservation in the MOGD system to utilize at least a portion of the reactor exotherm heat value by exchanging hot reactor effluent from one or more reactors with a fractionator stream to vaporize a liquid hydrocarbon distillation tower stream, such as the debutanizer reboiler. Optional heat exchangers may recover heat from the effluent stream prior to fractionation. Gasoline from the recycle conduit is pressurized by pump means and combined with feedstock, preferably at a mole ratio of about 1–2 moles per mole of olefin in the feedstock. It is preferred to operate in the distillate mode at elevated pressure of about 4200 to 7000 kPa (600–1000 psig).

The reactor system contains multiple downflow adiabatic catalytic zones in each reactor vessel. The liquid hourly space velocity (based on total fresh feedstock) is about 1 LHSV. In the distillate mode the inlet pressure to the first reactor is about 4200 kPa (600 psig total), with an olefin partial pressure of at least about 1200 kPa. Based on olefin conversion of 50% for ethene, 95% for propene, 85% for butene-1 and 75% for pentene-1, and exothermic heat of reaction is estimated at 450 BTU per pound of olefins converted. When released uniformly over the reactor beds, a maximum $\Delta T$ in each reactor is about 30° C. In the distilate mode the molar recycle ratio for gasoline is equimolar based on olefins in the feedstock, and the $C_3$–$C_4$ molar recycle is 0.5:1.

SORPTION/PREFRACTIONATOR OPERATION

The prefractionation system is adapted to separate volatile hydrocarbons comprising a major amount of $C_2$–$C_4$ olefins, and typically contains 10 to 50 mole % of ethene and propene each. In the detailed examples herein the feedstock consists essentially of volatile aliphatic components as follows: ethene, 24.5 mole %, propene, 46%; propane, 6.5%; 1-butene, 15% and butanes 8%, having an average molecular weight of about 42 and more than 85 mole % olefins.

The gasoline sorbent is an aliphatic hydrocarbon mixture boiling in the normal gasoline range of about 50° to 165° C. (125° to 330° F.), with minor amounts of $C_4$–$C_5$ alkanes and alkenes. Preferably, the total gasoline sorbent stream to feedstock weight ratio is greater than about 3:1; however, the content of $C_3^+$ olefinic components in the feedstock is a more preferred measure of sorbate to sorbent ratio. Accordingly, the process may be operated with a mole ratio of about 0.2 moles to about 10 moles of gasoline per mole of $C_3^+$ hydrocarbons in the feedstock, with optimum operation utilizing a sorbent:sorbate molar ratio about 1:1 to 1.5:1.

It is understood that the various process conditions are given for a continuous system operating at steady state, and that substantial variations in the process are possible within the inventive concept. In the detailed examples, metric units and parts by weight are employed unless otherwise specified.

Figure 3:
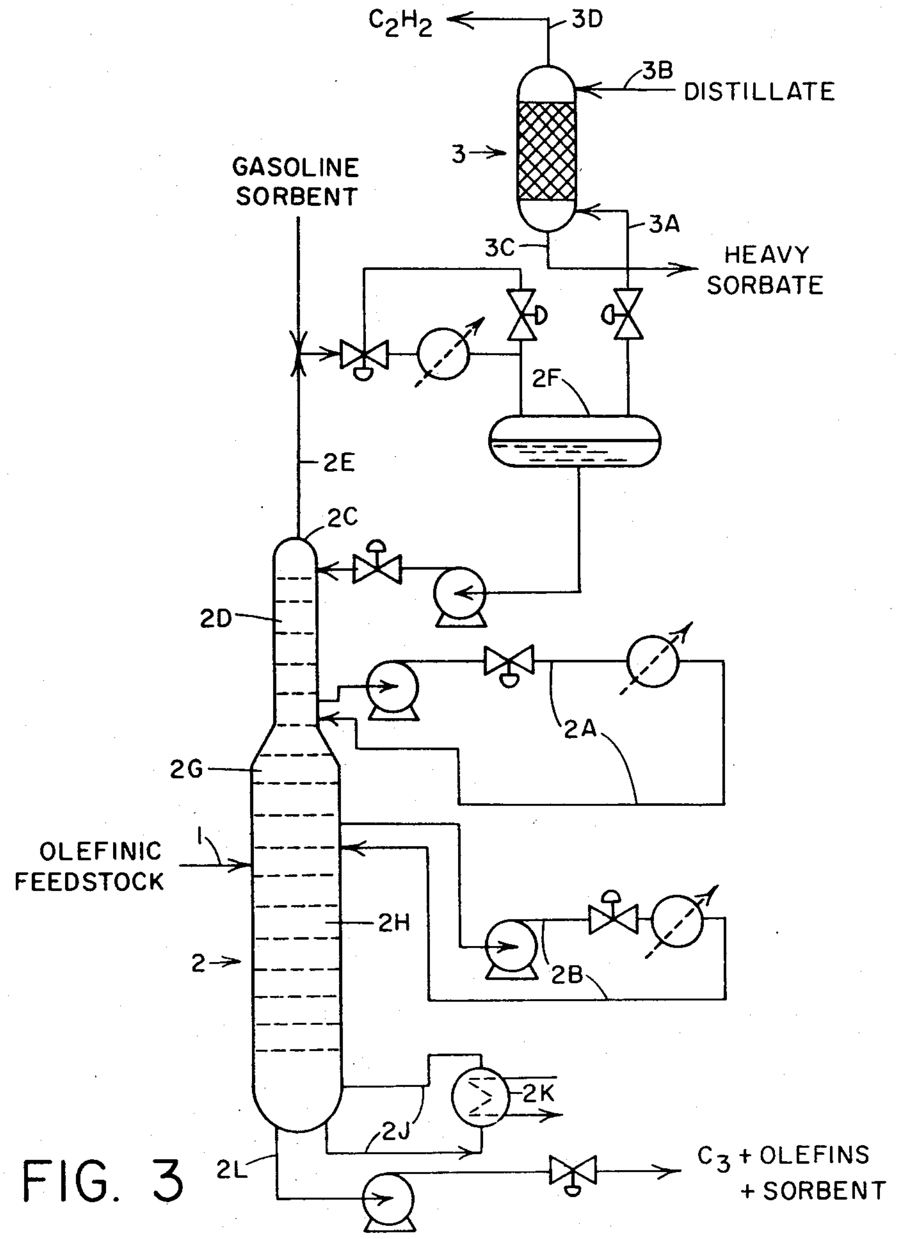
FIG. 3 is equipment layout and process flow for the prefractionation sorption system.

Referring to FIG. 3, olefinic feedstock is introduced to the system through a feedstock inlet 1 connected between stages of a fractionating sorption tower 2 wherein gaseous olefinic feedstock is contacted with liquid sorbent in a vertical fractionation column operating at least in the upper portion thereof in countercurrent flow. Effectively this unit is a $C_2/C_3^+$ splitter. Design of sorption equipment and unit operations are established chemical engineering techniques, and generally described in Kirk-Othmer "Encyclopedia of Chemical Technology" 3rd Ed. Vol. 1 pp. 53–96 (1978) incorporated herein by reference. In conventional refinery terminology, the sorbent stream is sometimes known as lean oil.

Sorpton tower 2, as depicted, has multiple contact zones, with the heat of absorption being removed via interstage pump around cooling means 2A, 2B. The liquid gasoline sorbent is introduced to the sorption tower through an upper inlet means 2C above the top contact section 2D. It is preferred to mix incoming liquid sorbent with outgoing splitter overhead ethylene-rich gas from upper gas outlet 2E and to pass this multiphase mixture into a phase separator 2F, operatively connected between the primary sorption tower 2 and a secondary sponge absorber 3. Liquid sorbent from separator 2F is then pumped to the upper liquid inlet 2C for countercurrent contact in a plate column or the like with upwardly flowing ethylene rich vapors. Liquid from the bottom of upper contact zone 2D is pumped to a heat exchanger in loop 2A, cooled and returned to the tower above intermediate contact zone 2G, again cooled in loop 2B, and returned to the tower above contact zone 2H, which is located below the feedstock inlet 1. Under tower design conditions of about 2100 kPa (300 psia), it is preferred to maintain liquid temperature of streams entering the tower from 2A, 2B and 2F at about 40° C. (100° F.). The lower contact zone 2H provides further fractionation of the olefin-rich liquid. Heat is supplied to the sorption tower by removing liquid from the bottom via reboiler loop 2J, heating this stream in heat exchanger 2K, and returning the reboiled bottom stream to the tower below contact zone 2H.

The liquid sorbate-sorbent mixture is withdrawn through bottom outlet 2L and pumped to storage or to olefins recovery or to reaction. This stream is suitable for use as a feedstock in an olefins oligomerization unit or may be utilized as fuel products. Ethylene rich vapor from the primary sorption tower is withdrawn via separator 2F through conduit 3A.

Distillate lean oil is fed to the top inlet 3B of sponge absorber 3 under process pressure at ambient or moderately warm temperature (e.g. 40° C.) and distributed at the top of a porous packed bed, such as Raschig rings, having sufficient bed height to provide multiple stages. The liquid rate is low; however, the sponge absorber permits sorption of about 25 wt. percent of the distillate weight in $C_3^+$ components sorbed from the ethylene-rich stream. This stream is recovered from bottom outlet 3C. It is understood that the sorbate may be recovered from mixture with the sorbent by fractionation and the sorbent may be recycled or otherwise utilized. High purity ethylene is recovered from the system through gas outlet 3D and sent to storage, further processing or conversion to other products.

The sorption towers depicted in the drawing employ a plate column in the primary tower and a packed column in the secondary tower, however, the fractionation equipment may employ vapor-liquid contact means of various designs in each stage including packed beds of Raschig rings, saddles or other porous solids or low pressure drop valve trays (Glitsch grids). The number of theoretical stages will be determined by the feedstream composition, liquid:vapor (L/V) ratios, desired recovery and product purity. In the detailed example herein, 17 theoretical stages were employed in the primary sorption tower and 8 stages in the sponge absorber, with olefinic feedstock being fed between the 7th and 9th stages of the primary sorption tower.

Examples 1 to 9 are based on the above-described feedstock at 40° C. (100° F.) and 2100 kPa (300 psia)

supplied to stage 9 of the primary sorption tower. Gasoline is supplied at 85° C. (185° F.) and 2150 kPa (305 psia), and distillate lean oil is supplied at 40° C. and 2100 kPa. Table I shows the conditions at each stage of the primary sorption tower, and Table II shows the conditions for the sponge absorber units for Example 1 (2 moles gasoline/mole of olefin in feedstock).

TABLE I

| Stage | Heat In KW/MT | Temperature (°C.) | Liquid/Vapor (L/V) Mole Ratio | Pressure (kPa) |
|---|---|---|---|---|
| 1 (top) | −121. + 362(1) | 37.8 | 6.947 | 2068.5 |
| 2 | | 38.5 | 2.245 | 2103.0 |
| 3 | | 39.7 | 2.222 | 2103.7 |
| 4 | | 42.3 | 2.227 | 2104.4 |
| 5 | | 47.2 | 2.221 | 2105.1 |
| 6 | | 54.2 | 2.185 | 2105.8 |
| 7 | −29.(2) | 57.6 | 2.216 | 2106.5 |
| 8 | | 65.3 | 1.864 | 2107.2 |
| 9 | −820. + 120(3) | 59.9 | 2.447 | 2107.9 |
| 10 | | 67.7 | 1.954 | 2108.6 |
| 11 | | 71.8 | 1.814 | 2109.3 |
| 12 | | 74.1 | 1.743 | 2110.0 |
| 13 | | 75.4 | 1.704 | 2110.7 |
| 14 | | 77.0 | 1.684 | 2111.4 |
| 15 | | 80.5 | 1.644 | 2112.1 |
| 16 | | 92.3 | 1.541 | 2112.8 |
| 17 (bottom) | 400.(4) | 136.2 | 0.872 | 2116.3 |

(1)Condenser Duty & Lean Oil
(2)1st Heat Removal Duty
(3)2nd Heat Removal Duty & Lean Oil
(4)Reboiler Duty, based on metric tons (MT) of feedstock

TABLE II

| Stage | Heat In (KW/MT) | Temperature (°C.) | Liquid/Vapor (L/V) Mole Ratio | Pressure (kPa) |
|---|---|---|---|---|
| 1 | 2.9(1) | 42.8 | 0.045 | 1999.6 |
| 2 | | 42.3 | 0.046 | 2000.2 |
| 3 | | 41.8 | 0.046 | 2000.9 |
| 4 | | 41.4 | 0.047 | 2001.6 |
| 5 | | 41.2 | 0.047 | 2002.3 |
| 6 | | 40.9 | 0.048 | 2003.0 |
| 7 | | 40.6 | 0.050 | 2003.7 |
| 8 | 32.8(2) | 40.1 | 0.056 | 2004.4 |

(1)Distillate Lean Oil
(2)$C_2^=/C_3^=+$ Splitter Overhead

Based on the above design, the following data show the effects of varying the flow rate of gasoline absorbent in the primary tower $C_2/C_3+$ splitter overhead and the corresponding effects of varying the distillate lean oil rate in the secondary sponge absorber. These data are shown in Table III, which give the ethylene ($C_2^=$) recovery and purity from each of the primary and secondary sorption units.

TABLE III

| Example No. | Gasoline Mole Ratio (1) | Distillate Mole Ratio | C2/C3+ Splitter Overhead: C2 = Recovery % | C2/C3+ Splitter Overhead: C2 = Purity MOL % | C2/C3+ Splitter Overhead: C2 = Purity WT % | Sponge Absorber Overhead: C2 = Recovery % | Sponge Absorber Overhead: C2 = Purity MOL % | Sponge Absorber Overhead: C2 = Purity WT % |
|---|---|---|---|---|---|---|---|---|
| 1 | 2:1 | 0.013 | 99.92 | 98.21 | 95.24 | 98.37 | 99.18 | 97.91 |
| 2 | 1:1 | 0.013 | 99.94 | 85.16 | 77.74 | 98.32 | 86.43 | 78.39 |
| 3 | 1.5:1 | 0.013 | 99.93 | 96.43 | 92.56 | 98.37 | 97.45 | 95.53 |
| 4 | 3:1 | 0.013 | 99.90 | 98.40 | 95.46 | 98.35 | 99.36 | 98.16 |
| 5 | 4:1 | 0.013 | 99.88 | 98.42 | 95.45 | 98.32 | 99.39 | 98.40 |
| 6 | 2:1 | 0.006 | 99.92 | 98.21 | 95.24 | 99.02 | 98.98 | 97.48 |
| 7 | 2:1 | 0.01 | 99.92 | 98.21 | 95.24 | 98.68 | 99.09 | 97.67 |
| 8 | 2:1 | 0.019 | 99.92 | 98.21 | 95.24 | 97.77 | 99.31 | 98.40 |
| 9 | 2:1 | 0.025 | 99.92 | 98.21 | 95.24 | 97.17 | 99.43 | 98.65 |

(1) Gasoline Absorbent Rate Moles/Mole of Total Olefin in Feedstock.

In general, as the flow rate of lean oil increases, the ethylene recovery decreases, while the purity increases. The data for the splitter/absorber combination show that the excellent results are obtained with a gasoline mole ratio of at least 1:1 (based on $C_3+$ hydrocarbons). Such conditions will result in a $C_2^=$ recovery of greater than 98%. Purity of more than 99 mole % can be achieved with a gasoline mole ratio of at least 2:1.

A preferred sorbent source is olefinic gasoline and distillate produced by catalytic oligomerization according to U.S. Pat. No. 4,211,640 (Garwood & Lee) and U.S. patent application Ser. No. 488,834, filed Apr. 26, 1983 (Owen et al), incorporated herein by reference. The $C_3+$ olefin sorbate and gasoline may be fed directly to such oligomerization process, with a portion of recovered gasoline and distillate being recycled to the sorption fractionation system herein. Table IV shows the boiling range fraction composition for typical gasoline and distillate sorbents.

TABLE IV

| Lean Oil Compositions (MOL %) | Gasoline | Distillate |
|---|---|---|
| Propane | 0.00 | 0 |
| Isobutane | 0.15 | 0 |
| 1-Butene | 0.12 | 0 |
| N—Butene | 0.59 | 0 |
| Isopentane | 2.60 | 0 |
| 1-Pentene | 0.24 | 0 |
| N—Pentane | 0.24 | 0 |
| 52–82° C. | 11.24 | 0 |
| 82–104° C. | 22.02 | 0 |
| 104–127° C. | 23.54 | 0.02 |
| 127–138° C. | 11.23 | 0.09 |
| 138–149° C. | 10.47 | 0.43 |
| 149–160° C. | 8.70 | 2.00 |
| 160–171° C. | 1.54 | 2.13 |
| 171–182° C. | 0.92 | 7.06 |
| 182–193° C. | 0.31 | 11.16 |
| 193–204° C. | 0.10 | 14.53 |
| 204–216° C. | 0.01 | 8.36 |
| 216–227° C. | 0.00 | 8.56 |
| 227–238° C. | 0 | 7.56 |
| 238–249° C. | 0 | 6.50 |
| 249–260° C. | 0 | 6.00 |
| 260–271° C. | 0 | 4.30 |
| 271–293° C. | 0 | 5.10 |
| 293–316° C. | 0 | 4.13 |
| 316–338° C. | 0 | 3.24 |
| 338–360° C. | 0 | 3.17 |
| 360–382° C. | 0 | 4.63 |
| 382–404° C. | 0 | 0.91 |
| 404–438° C. | 0 | 0.11 |

The sponge absorber may be constructed in a separate unit, as shown, or this operation may be conducted in an integral shell vessel with the main fractionation unit. In the alternative integral design, the rich sponge oil may be recovered from the upper contact zone as a separate stream, or the heavy distillate sorbent may be intermixed downwardly with gasoline sorbent and withdrawn from the bottom of the main fractionation zone.

The stream components of the olefinic feedstock and other main streams of the sorption/prefractionator unit and reactor feedstreams are set forth in Table V, based on parts by weight per 100 parts of feedstock.

TABLE V

| Component wt. % | Fresh Feed | Main $C_1/C_2$ Fract. | Gasoline Recycle | Sponge Absorber Feed | Sorption Reflux | Distillate Sorbent | Ethene Product | Sponge Sorber Bottoms | Reactor Inlet |
|---|---|---|---|---|---|---|---|---|---|
| $C_1$ | — | — | — | — | — | — | — | — | — |
| $C_2^=$ | 16.3 | 50.5 | — | 16.3 | 34.2 | — | 16.0 | 0.3 | — |
| $C_2$ | — | — | — | — | — | — | — | — | — |
| $C_3^=$ | 45.9 | 0.5 | — | 0.06 | 0.4 | — | 0.05 | — | 45.9 |
| $C_3$ | 6.8 | 0.02 | — | — | 0.02 | — | — | — | 6.8 |
| i-$C_4$ | 7.7 | 0.04 | 0.3 | 0.02 | 0.4 | — | 0.01 | — | 8.0 |
| $C_4^=$ | 20.0 | 0.03 | 0.2 | 0.01 | 0.2 | — | — | — | 20.1 |
| $NC_4$ | 3.3 | 0.12 | 1.0 | 0.04 | 1.0 | — | 0.03 | — | 4.2 |
| i-$C_5$ | — | 0.3 | 5.4 | 0.09 | 5.6 | — | 0.06 | 0.04 | 5.2 |
| $C_5$ | — | 0.6 | 12.5 | 0.2 | 12.8 | — | 0.1 | 0.09 | 12.2 |
| n-$C_5$ | — | 0.02 | 0.5 | — | 0.5 | — | — | — | 0.5 |
| 125–330° F. | — | 1.4 | 270.8 | 0.4 | 272.8 | 0.05 | — | 0.5 | 270.7 |
| 330° F.+ | — | — | 15.6 | — | 14.1 | 3.5 | — | 3.5 | 15.6 |
| Stream No. | 1 | 2E | 50L | 3A | 2F liq | 3B | 3D | 3C | 30F |

More than 98% of ethylene is recovered in the above example from the feedstock, and the gas product requires little additional treatment to raise its purity from 99.2 mol% to polymar grade.

In the refining of petroleum or manufacture of fuels from fossil materials or various sorces of hydrocarbonaceous sources, an olefinic mixture is often produced. For instance, in cracking heavier petroleum fractions, such as gas oil, to make gasoline or distillate range products, light gases containing ethene, propene, butene and related aliphatic hydrocarbons are produced. It is known to recover these valuable by-products for use as chemical feedstocks for other processes, such as alkylation, polymerization, oligomerization, LPG fuel, etc. Ethylene is particularly valuable as a basic material in the manufacture of polyethylene and other plastics, and its commercial value is substantially higher as a precursor for the chemical industry than as a fuel component. Accordingly, it is desirable to separate ethylene in high purity for such uses.

A typical byproduct of fluid catalytic cracking (FCC) units is an olefinic stream rich in $C_2$–$C_4$ olefins, usually in mixture with lower alkanes. Ethylene can be recovered from such streams by conventional fractionation means, such as cryogenic distillation, to recover the $C_2$ and $C_3+$ fractions; however, the equipment and processing costs are high.

There are several reasons for not converting the ethylene to distillate and gasoline. The high pressure and low space velocity required for any significant conversion (on the order of 75 wt. %) would require a separate reactor train and at least one additional tower. This would substantially increase the capital cost of the unit. Converting the ethylene with the propylene/butylene stream would result in an ethylene conversion of about 20 wt. %. Additionally, the value of polymer grade ethylene may be much higher than the gasoline and distillate which would be produced if the ethylene were to be converted. Finally, there would be difficulty in scheduling the regenration section to regenerate both the ethylene conversion and propylene/butylene conversion reactors.

While the invention has been described by specific examples and embodiments, there is no intent to limit the inventive concept except as set forth in the following claims.

What is claimed is:

1. A continuous catalytic process for converting a fraction of olefinic feedstock comprising ethylene and $C_3+$ olefins to heavier liquid hydrocarbon product comprising the steps of (a) prefractionating the olefinic feedstock to obtain a gaseous stream rich in ethylene and a liquid stream containing $C_3+$ olefin;

(b) Vaporizing and contacting the liquid stream from the prefractionating step with hydrocarbon conversion oligomerization catalyst in a catalytic reactor system to provide a heavier hydrocarbon effluent stream comprising distillate, gasoline and lighter hydrocarbons;

(c) fractionating the effluent stream to recover distillate, gasoline and lighter hydrocarbons separately;

(d) recycling at least a portion of the recovered gasoline as a liquid sorption stream to prefractionating step (a); and (e) further reacting the recycled gasoline together with sorbed $C_3+$ olefin in the catalytic reactor system of step (b).

2. The process of claim 1 comprising the additional step of contacting the ethylene rich gaseous stream from prefractionating step (a) with a minor amount of distillate liquid absorbent to provide a purified ethylene product.

3. The process of claim 2 wherein the distillate liquid is a recycled distillate from fractionating step (c) and wherein said distillate absorbent liquid is combined with reactor effluent from the catalytic reactor prior to fractionating step (c).

4. The process of claim 2 wherein the purified ethylene product has an average molecular weight not greater than 28.5.

5. The process of claim 1 wherein the recycled gasoline comprises $C_5+$ olefinic components.

6. The process of claim 1 wherein the oligomerization catalyst comprises a shape-selective medium pore crystalline aluminosilicate zeolite having a silica:alumina mole ratio of at least 12 and a constraint index of about 1 to 12, and wherein olefins are oligomerized in the essential absence of hydrogen.

7. The process of claim 6 wherein the catalyst comprises HZSM-5 having an acid cracking activity of about 160 to 200.

8. The process of claim 1 wherein the olefinic feedstock comprises about 10 to 50 mole % ethylene and 10 to 50 mole % propene.

9. The process of claim 1 wherein gasoline is recycled at a weight ratio to olefinic feedstock of at least about 3:1.

* * * * *